United States Patent [19]

Percarpio

[11] 4,155,350

[45] May 22, 1979

[54] INTEGRATED BLOOD COLLECTION SYSTEM

[75] Inventor: Edward P. Percarpio, N. Haledon, N.J.

[73] Assignee: Becton, Dickinson and Company, East Rutherford, N.J.

[21] Appl. No.: 786,080

[22] Filed: Apr. 11, 1977

[51] Int. Cl.² .............................................. A61B 5/14
[52] U.S. Cl. .................................................. 128/764
[58] Field of Search ................. 128/2 F, DIG. 5, 272, 128/218 R, 218 D, 218 DA, 218 N, 218 NV, 276

[56] References Cited

U.S. PATENT DOCUMENTS

| | | | |
|---|---|---|---|
| 1,526,595 | 2/1925 | Gillman | 128/DIG. 5 |
| 2,734,649 | 2/1956 | Callahan et al. | 128/272 X |
| 3,055,367 | 9/1962 | Thorstad | 128/272 |
| 3,106,206 | 10/1963 | Barr, Sr. et al. | 128/DIG. 5 |
| 3,877,465 | 4/1975 | Miyake | 128/2 F |
| 3,965,889 | 6/1976 | Sachs | 128/2 F |

FOREIGN PATENT DOCUMENTS

| | | | |
|---|---|---|---|
| 2529445 | 1/1977 | Fed. Rep. of Germany | 128/DIG. 5 |
| 272034 | 2/1930 | Italy | 128/DIG. 5 |

*Primary Examiner*—John D. Yasko
*Attorney, Agent, or Firm*—Kane, Dalsimer, Kane, Sullivan & Kurucz

[57] ABSTRACT

A blood collection assembly for taking a blood sample from a blood source. The assembly includes a double ended hollow cannula open at both ends and mounted in a hub. A hollow evacuated blood collection tube is provided having an opening at one end. A stopper is mounted in the open end of the tube to seal the tube and maintain the vacuum therein. The hub includes a gripping surface for facilitating the holding and directing both ends of the cannula, one end into communication with the blood source and the other end into communication with the evacuated collection tube. The cannula is coupled with the stoppered tube in position for insertion of the other end thereof into communication with the interior of the stoppered tube after the one end has been connected to the blood source to permit blood to flow through the cannula into the tube for collection.

3 Claims, 8 Drawing Figures

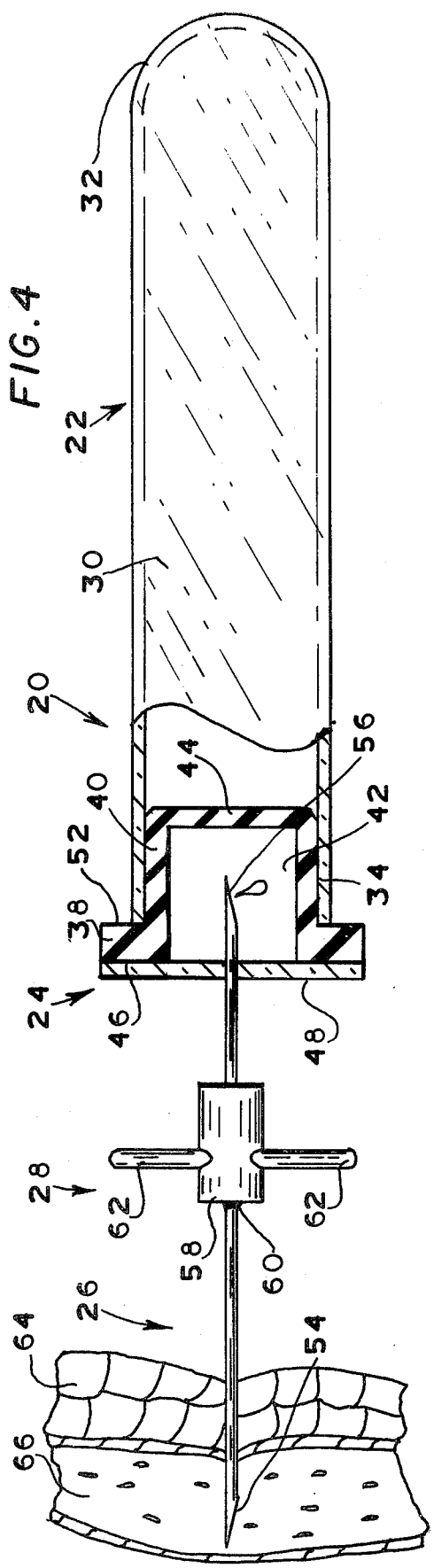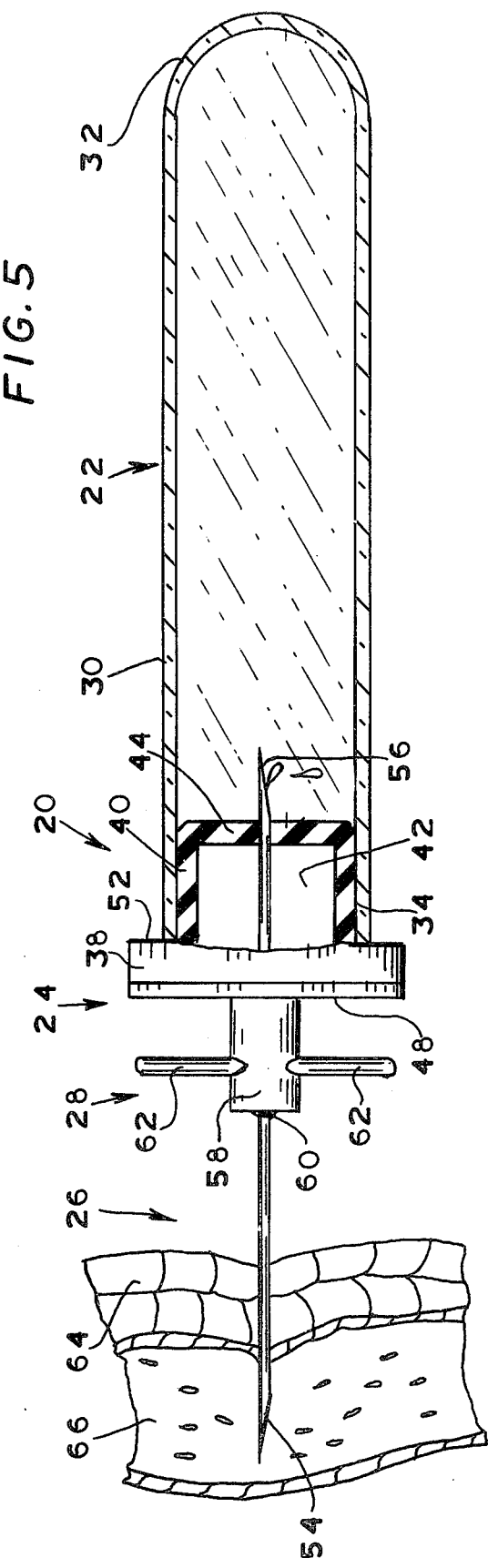

INTEGRATED BLOOD COLLECTION SYSTEM

BACKGROUND OF THE INVENTION

Through the years there have been numerous systems developed for the collection of blood samples. The most common method today is the use of a double ended needle in combination with an evacuated tube and a holder for guiding the needle and tube into coupling relationship. The basic system is described in U.S. Pat. No. 2,460,641 and initiated a new technique for collecting blood samples and one which to a large extent has replaced the traditional method of collecting each blood sample in a separate syringe.

The system is now well known and utilizes basically a three part arrangement with many variations having been developed over the years to improve each of the three basic components.

The first part is a double ended needle mounted in a hub. Various types of valves have been designed for this part to operate automatically and normally for collection of successive samples in successive collection containers.

The second part, the collection container, is in the form of a partially or fully evacuated tube which may or may not contain medicament to act with the blood when it is collected in the tube. A rubber stopper is generally used to close the open end of the tube and maintain the vacuum therein. The stopper is of a self-sealing puncturable material to facilitate coupling and uncoupling of the needle assembly with the tube during use. There have been different types of stoppers developed throughout the years to assist in this coupling and uncoupling action while maintaining the vacuum prior to coupling and maintaining the integrity of the interior in the tube after sampling has been completed.

The third component of the system is generally identified as a holder and is adapted for removable attachment to the hub holding the cannula such as by threaded interengagement. The holder acts as a convenient means for holding the assembly during use and also acts as a guide for the tube so that it can easily be into alignment for penetration by the needle and also for removal of the tube and introduction of a subsequent tube as a series of samples are collected. Once again, various improvements have been developed through the years to provide better holders for better guideways, to improve the gripping surface for the operator and to form certain indicating positions to help the user determine of his relative positioning of the needle with respect to the tube.

These various improvements are designed to provide a dependable and efficient blood collection assembly of the evacuated tube type while maintaining low cost, including both the cost of manufacture and the cost of storage and ultimate use. Disposability is important in the medical instrument field today. Naturally, reduction in the number of parts reduces the total cost of the assembly and makes disposability more feasible, particularly in mass use. This is an important goal in the medical instrument field today.

SUMMARY OF THE INVENTION

With the above background in mind, it is among the primary objectives of the present invention to provide a complete unitary blood collection assembly. The unit includes a cannula, a low penetration force stopper and an evacuated collection tube. The need to assemble or utilize a separate holder with the needle assembly and the tube is eliminated. The entire assembly includes a uniquely designed stoppered evacuated tube and a coupled needle assembly and hub which are packaged together as a unit. No holder is required during manufacture, shipment, storage or use of the assembly.

The stopper is designed so that very low needle penetration force is required thus reducing the trauma to the patient and facilitating the efficient and easy operation of the unit. Furthermore, there is considerable freedom of movement of the needle with respect to the stopper so as to enable the use of a low angle to the vein of the patient upon penetration making previously difficult techniques more easy to accomplish.

The assembly provides a lower cost structure, since the holder is eliminated along with separate packaging for the needle assembly and evacuated tube components. Furthermore, the assembly is designed so that there is a greatly reduced length of the cannula required to puncture the stopper and enter the evacuated tube since the point of entry for the needle is relatively thin. This feature naturally adds to the ease and efficiency of operation as well.

Other features of the assembly include the provision of a winged hub with lateral projections to facilitate gripping and handling of the assembly during use, a thin diaphragm mounted on the hopper and spaced from the thin penetration portion of the stopper to provide a retaining chamber in the stopper. This chamber is designed to house the one end of the cannula which penetrates the diaphragm, is held in sealing engagement by the diaphragm, and thus couples the needle assembly with the tube with the tip of the needle in the chamber. Thus, the elements of the assembly are interconnected and any leakage through the cannula upon venipuncture is captured in the chamber in the stopper before penetration of the chamber through the bottom wall of the stopper and into the evacuated tube portion.

Alternatively, the penetration bottom wall of the stopper can be made thick enough to permit the open end of the cannula to be embedded therein. Thus, upon venipuncture, there will be no leakage from that open end prior to full penetration of the bottom wall of the stopper and into communication with the interior of the evacuated portion of the tube.

A further objective is to provide an integrated system that can be packaged as a unit in assembled condition in a conventional blister or vacuum packed container. Optionally, the system is designed so that a valve could be located over the end of the needle opposite to the venipuncture and to prevent leakage upon the initial venipuncture in a conventional and well known fashion. The valve would naturally operate to permit flow when the end of the needle punctures the bottom wall of the stopper into communication with the interior of the evacuated tube.

In summary, a blood collection assembly is provided for taking a blood sample from a blood source. The assembly includes a double ended hollow cannula open at both ends and mounted in a hub. A hollow blood collection tube having an opening at one end is provided. A stopper is mounted in the open end of the tube to seal the tube and maintain the vacuum therein. Coupling means is provided on the cannula and the stoppered tube for coupling the cannula with the stoppered tube in position for insertion of the other end thereof into communication with the interior of the stoppered tube after the one end has been connected to the blood source to permit blood to flow through the cannula into the tube for collection. Finally, gripping means is on the hub for facilitating the holding and directing both ends of the cannula, one end into communication with a blood source and the other end into communication with the evacuated blood collection tube.

With the above objectives among others in mind, reference is made to the attached drawings.

BRIEF DESCRIPTION OF THE DRAWINGS

FIG. 4 is a partially sectional side elevation view thereof showing the cannula penetrating a vein and prior to coupling with the interior of the evacuated tube;

FIG. 5 is a partially sectional side elevation view thereof showing the one end of the needle coupled with the vein and the other end coupled with the interior of the evacuated tube so that blood is being collected in the evacuated tube;

DESCRIPTION OF THE PREFERRED EMBODIMENTS

Figure 3:
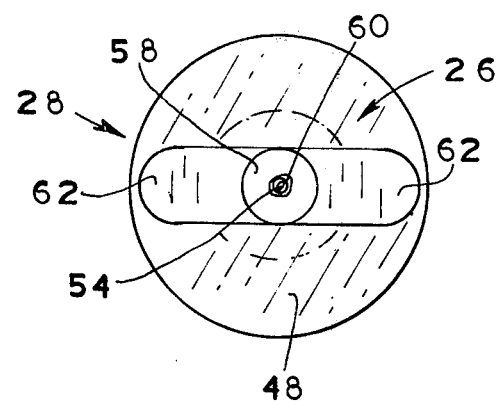
FIG. 3 is a top plan view thereof.
Figure 2:
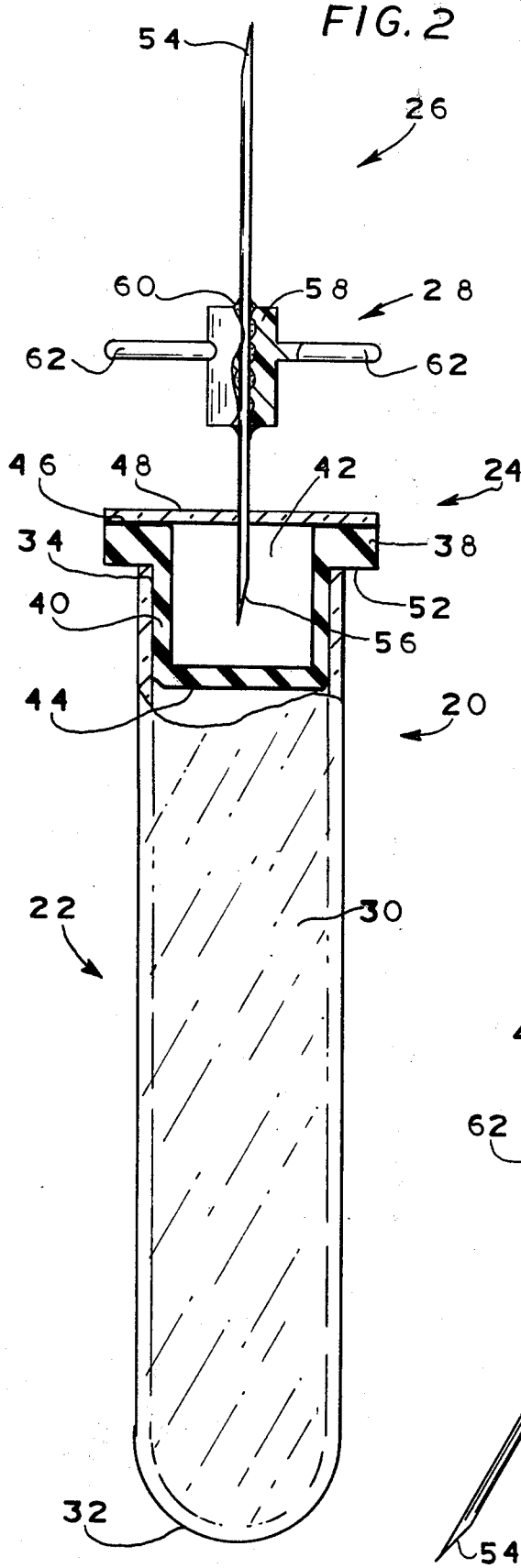
FIG. 2 is a partially sectional side elevation view thereof.
Figure 1:
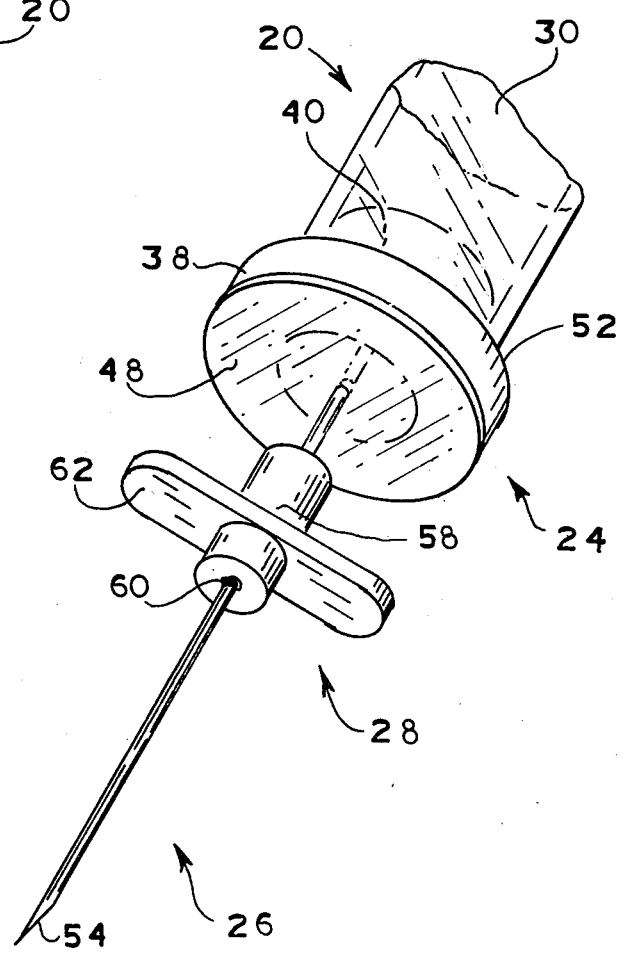
FIG. 1 is a fragmentary perspective view of the assembly of the invention.

Blood collection assembly 20 as depicted in the drawings includes an evacuated tube 22, a stopper 24, a double ended cannula 26, and a hub 28 on the cannula.

Tube 22 is a cylindrically shaped member with a hollow chamber 30 therein which is partially or fully evacuated and may, if desired, be filled with a medicament or other substance such as an anticoagulant. The tube has a closed bottom end 32 and an open top end 34. An annular rim 36 surrounds the top end 35. Tube 22 may be formed of glass or plastic or any conventional substitute therefor. It is constructed of a disposable material as are the remainder of the components of assembly 20.

Stopper 24 is preferably of self-sealing elastomeric material such as natural or synthetic rubber. The stopper is formed with an enlarged diameter head portion 38 and a lesser diameter body portion 40 extending from one side thereof. Both head portion 38 and bottom portion 40 are substantially tubular in configuration. The stopper is formed with a central recess 42 open at one end and terminating in a thin base portion 44 of the stopper sealing the bottom end of the stopper and forming the base for recess 42.

Figure 6:
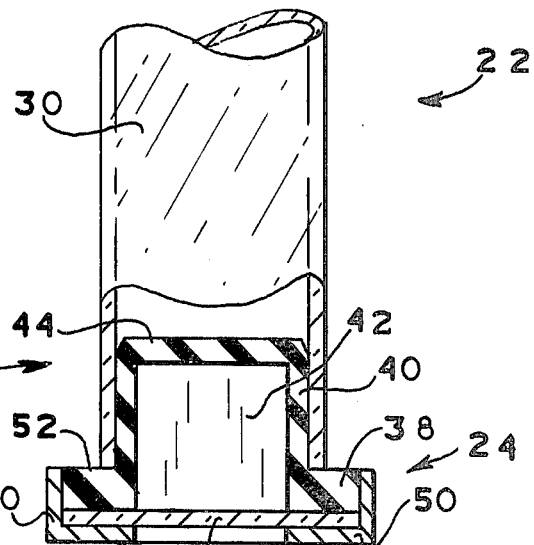
FIG. 6 is a fragmentary sectional elevation view of an alternative embodiment of the invention.

Positioned on the upper surface 46 of stopper 24 is a thin puncturable diaphragm 48 which can be formed of a conventional material such as rubber or plastic. The diaphragm 48 closes the opening to recess 42 to form a closed chamber and is held in position by a conventional adhesive or other well known means. For example, as shown in FIG. 6, alternatively, a cap support 50 can be used which may be frictionally or otherwise conventionally attached to the stopper and diaphragm to hold the diaphragm in position, such as by crimping. Conveniently, cap 50 can be formed of plastic or metal material and is formed to surround a portion of the head 38 of the stopper and couple the diaphragm to the upper surface 46 of head 38.

Stopper 24 is positioned in tube 20 with the exterior side walls of body 40 frictionally engaging with inner adjacent surface of open end portion 34 of tube 22. The stopper is inserted until the under surface 52 of head 38 seats on rim 36 of the tube. Thus, the stopper is positioned in tight interengagement in the tube and normally seals the opening and maintains the vacuum in chamber 30.

Cannula 25 is a conventional double ended cannula with a pointed forward tip 54 adapted for venipuncture purposes and a pointed rear tip 56 adapted for introduction to the tube. A through passageway extends from end to end in cannula 26 which is open at both ends. A hub 28 is mounted intermediate the ends of the cannula by conventional means such as epoxy. The cannula 26 may be formed of a conventional inexpensive disposable metal material and hub 28 of a conventional disposable plastic material. The two parts can be interconnected by a convenient means such as epoxy.

Hub 28 has a tubular body portion 58 with a central passageway 60 therethrough for passage of the needle 26 and interengagement therewith. Extending laterally from body portion 58 are a pair of opposed lateral projections or wings 62 in approximately diametrically opposite angular locations with respect to one another. Naturally the number and size of wings 62 are matters of choice and convenience.

In the normal packaged condition, ready for use, end 56 extends through diaphragm 48 and is housed in recess 42 which is sealed by bottom wall 44 of the stopper and diaphragm 48 which sealingly engages with cannula 26. Thus, the assembled cannula 26 and tube 28 is coupled in prepackaged condition and is ready for use when the package is opened.

The sequence of operation of the assembly is depicted in FIGS. 4 and 5. Initially, venipuncture end 54 is passed through the patient'w body tissue 64 and into a vein 66 thus causing blood to flow through cannula 26 and enter recess 42 as depicted in FIG. 4 thereby indicating a successful venipuncture and also capturing any leakage of blood so that there is no contamination of the surrounding area. Visual observance of the successful venipuncture can be accomplished by providing a transparent portion on the wall surface forming recess 42.

Thereafter, as depicted in FIG. 5, the tube 22 and needle 26 are axially shifted with respect to one another so that tip 56 passes through the bottom wall 44 of the stopper and enters the evacuated chamber 30 within the tube. Blood can now freely flow from vein 66 into tube 30 for collection of the appropriate sample as depicted in FIG. 5.

When the sample has been collected, the venipuncture end 52 is removed from the patient and the needle 26 removed from stopper 24 whereupon bottom wall 44 of self-sealing material seals the chamber 30 and the samples can then be transferred in the tube for testing purposes.

Therefore, a blood sample can be taken with a minimum number of components, a cannula, and a stoppered evacuated collection tube. With the present assembly, there is no longer any need to separately assemble a holder, a cannula and a tube prior to use. All that is required is that the package be opened, the assembled tube and cannula be utilized as described above with no necessity of preassembly.

Furthermore, since the stopper bottom wall 44 is thin, there is very low needle penetration force required thus reducing the trauma that could occur to the patient by the use of extreme force in any respect on the part of the operator.

Furthermore, since cannula 26 is free to pivot with respect to stopper 24 due to the fact that cannula end 56 is free of lateral restriction to a considerable degree and the cannula is held merely by its engagement with the thin diaphragm 48 at the top of the stopper, cannula 26 and hub 28 can tip and pivot with respect to the stoppered tube at least until tip 56 comes into contact with the side walls of the recess 42. At any point in this pivoting action, the needle is free to penetrate bottom wall 44 with the same result in that communication is achieved with chamber 30.

The overall assembly 20 is of lower cost than those presently available since the necessity for a holder is eliminated as well as separate packaging for the needle and tube components and the requirement of assembly at the site of use. Also, the length of needle 26 can be reduced since there is only a short travel distance required until puncture of base 44 can be accomplished. This is due to the fact that base 44 of the stopper is relatively thin in cross section.

It should also be noted that the wings 62 on the hub form a convenient gripping surface to assist in facilitating ease of penetration of cannula 26 through bottom wall 44. Thus, the wings permit ease of gripping of the cannula and hub and provide an aid in achieving relative movement in the axial direction between the cannula and the evacuated tube to achieve the necessary communication therebetween after a venipuncture has been accomplished. Also, the ability to grip the hub with the assistance of wings 62 aids in accomplishing the venipuncture in a quick and efficient manner without the necessity of undue force.

Naturally, if it is desirable a valve can be positioned on the rear end 56 of cannula 26 to prevent initial flow of blood after the venipuncture has been accomplished. The valve can be automatic such as a conventional elastomeric sleeve of puncturable self-sealing material which would permit tip 56 to puncture the sleeve and then bottom wall 44 when it is desired to connect with chamber 30. Thus, there will be no leakage until tip 56 has been passed through bottom wall 44.

Figure 7:
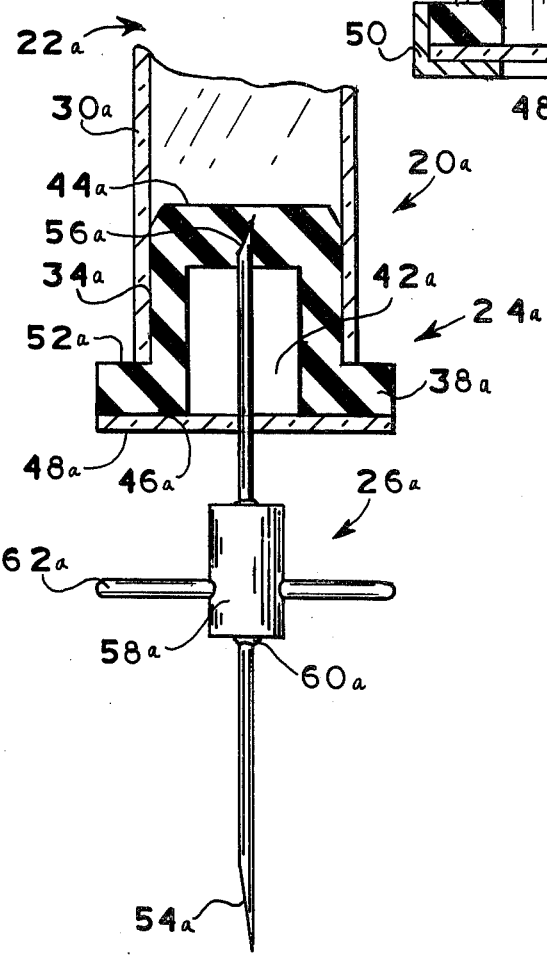
FIG. 7 is a fragmentary partially sectional elevational view of a second alternative embodiment of the invention showing the assembly before venipuncture.

FIGS. 6 and 7 show an alternative embodiment of the invention and like parts bear like numerals with the addition of the subscript a. The difference in blood collection assembly 20a resides in the thickness of bottom wall 44a of stopper 24a. It has a much greater thickness than the bottom wall 44 of the previously discussed embodiment and is designed for use with the same type of double ended needle assembly 26a as employed in connection with the above embodiment. Thus, when utilizing a needle assembly 26a with the thicker base wall 44a, the tip 56a of needle assembly 26a is initially embedded in diaphragm 44a. This condition is depicted in FIG. 6. This is in contrast to the previous embodiment where the tip 56 is spaced from base wall 44 in the recess 42. Thus, with needle assembly 20a, upon venipuncture, there will be no unwanted blood flow into the chamber recess 42a since tip 56a is sealed in embedded position in base wall 44a. This embodiment is particularly useful if a shut-off valve on the needle assembly is not being utilized and also where the recess 42 is not being used as a chamber for indicating a successful venipuncture.

Figure 8:
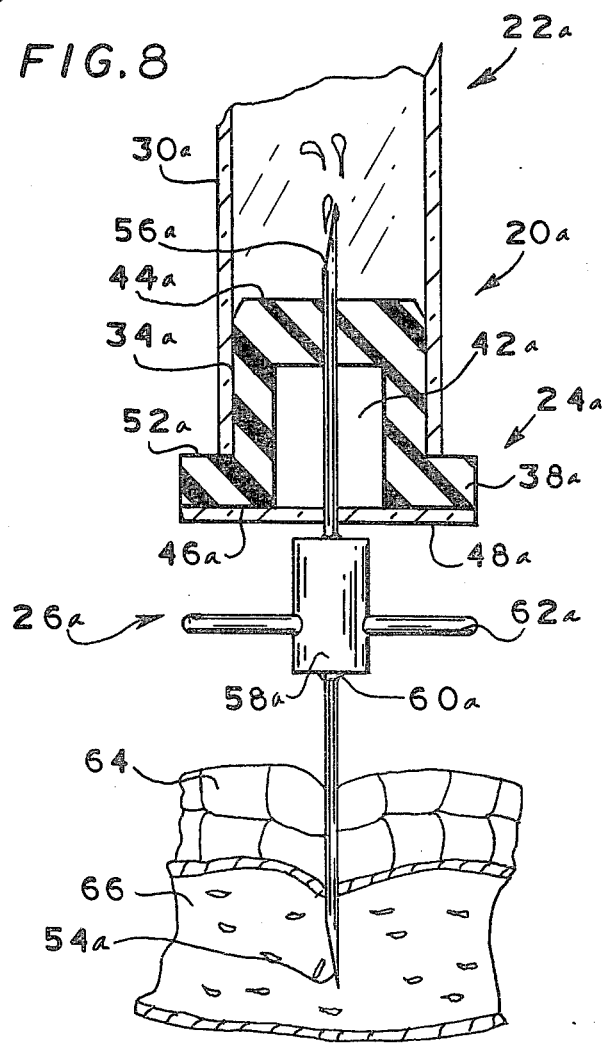
FIG. 8 is a fragmentary partially sectional elevational view thereof showing the assembly after venipuncture.

After venipuncture, the tip 56 can be passed through base wall 44 into communication with the evacuated chamber in the tube for collection of the sample as depicted in FIG. 8.

While the presently depicted device has been described in connection with collecting blood samples, it can be readily envisioned how the same assembly can be used for collection of blood from other sources and collection of other fluid samples including other human or animal body fluids.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims:

I claim:

1. A blood collection assembly for taking a blood sample from a blood source comprising:
   a double ended hollow cannula open at both ends and mounted in a hub;
   a hollow evacuated blood collection tube having an opening at one end;
   a stopper mounted in the open end of the tube to seal the tube and maintain the vacuum therein;
   gripping means on the hub for facilitating the holding and directing both ends of the cannula, one end into communication with a blood source and the other end into communication with the evacuated blood collection tube;
   coupling means on the cannula and the stoppered tube for coupling the cannula with the stoppered tube in position for insertion of the other end thereof into communication with the interior of the stoppered tube after the one end has been connected to the blood source to permit blood to flow through the cannula into the tube for collection thereof;
   the stopper being formed with an enlarged head portion of larger outer diameter and a body portion of lesser diameter extending therefrom, the outer surface of the body portion adapted to be frictionally interengaged with the inner surface of the open end of the evacuated tube for sealing engagement therewith;
   a central recess formed in the stopper terminating adjacent the bottom end thereof so as to form a thin bottom wall at the end of the body distal from the head for ease of penetration of the cannula therethrough;
   a diaphragm on the stopper spaced from the thin bottom wall so as to cooperate with the recess to form a chamber between the diaphragm and the bottom wall;
   the diaphragm having the other end of the cannula extending therethrough in coupled relationship therewith thereby providing a coupled interengaged stoppered tube and cannula prior to use;
   the diaphragm being in sliding sealing engagement with the cannula to permit the cannula to penetrate through the bottom wall of the stopper and into communication with the interior of the evacuated tube for collection of a blood sample when the one end of the tube is inserted into a blood source.

2. The invention in accordance with claim 1 wherein the diaphragm is seated in fixed position on the exposed upper surface of the head of the stopper, and a retaining cap to couple the diaphragm and the head of the stopper with the diaphragm in position to close the opening to the recess and form the chamber in the stopper.

3. The invention in accordance with claim 1 wherein the tip of the other end of the cannula is spaced from the bottom wall of the stopper and the diameter of the recess is substantially greater than the outer diameter of the cannula in position therein thereby permitting the cannula to pivot with respect to the diaphragm so as to permit the relative pivoting of the evacuated tube and the cannula to accommodate different angular positions with respect to the blood source, the angle of pivot being determined by the area of the bottom wall of the stopper with the other end of the needle being able to penetrate into the evacuated tube through the bottom wall at a point thereof to provide a passageway from the blood source to the interior of the tube.

* * * * *